(12) United States Patent
Kwiatkowski et al.

(10) Patent No.: US 6,835,836 B2
(45) Date of Patent: Dec. 28, 2004

(54) DICHLORINATED HETEROCYCLIC COMPOUNDS AND METHODS OF SYNTHESIS

(75) Inventors: Stefan Kwiatkowski, Lexington, KY (US); Miroslaw Golinski, Lexington, KY (US)

(73) Assignee: R.T. Alamo Ventures I, LLC, Beverly Hills, CA (US)

( * ) Notice: Subject to any disclaimer, the term of this patent is extended or adjusted under 35 U.S.C. 154(b) by 0 days.

(21) Appl. No.: 10/781,531

(22) Filed: Feb. 18, 2004

(65) Prior Publication Data

US 2004/0229906 A1 Nov. 18, 2004

Related U.S. Application Data

(62) Division of application No. 10/281,563, filed on Oct. 28, 2002, now Pat. No. 6,727,262.

(60) Provisional application No. 60/361,146, filed on Mar. 1, 2002.

(51) Int. Cl.$^7$ ............................................. C07D 215/36
(52) U.S. Cl. ..................................................... 546/155
(58) Field of Search ......................................... 546/155

(56) References Cited

U.S. PATENT DOCUMENTS 6,307,050 B1 * 10/2001 Kwiatkowski et al. ...... 546/155

* cited by examiner

*Primary Examiner*—Patricia L Morris
(74) *Attorney, Agent, or Firm*—Medlen & Carroll, LLP (57) ABSTRACT

Compositions of the present invention comprise dichlorinated heterocyclic compounds, including dichloroflosequinan. The methods of the present invention also comprise the synthesis of dichloroflosequinan.

1 Claim, 7 Drawing Sheets

| CAT. # | TARGET | BATCH*SPP. | n= | CONC. | % | †% INHIBITION -100 -50 0 50 100 | IC$_{50}$ | K$_1$ | n$_H$ | R |
|---|---|---|---|---|---|---|---|---|---|---|
| 154000 | PHOSPHODIESTERASE PDE4 | 44171 HUM | 2 | 30 µM | 36 | | | | | |
| | | | 2 | 10 µM | 22 | | | | | |
| | | | 2 | 3 µM | 2 | | | | | |
| ♦ 156000 | PHOSPHODIESTERASE PDE5 | 43974 HUM | 2 | 100 µM | 32 | | | | | |
| | | | 2 | 100 µM | 69 | | 127 µM | | | |
| | | 44172 HUM | 2 | 1000 µM | 50 | | | | | |
| | | | 2 | 300 µM | 76 | | | | | |
| | | | 2 | 100 µM | 60 | | | | | |
| | | | 2 | 30 µM | 32 | | | | | |
| | | | 2 | 10 µM | 18 | | | | | |
| | | | 2 | 3 µM | 6 | | | | | |
| 156100 | PHOSPHODIESTERASE PDE6 | 43975 BOV | 2 | 100 µM | 36 | | | | | |

*BATCH: REPRESENTS COMPOUNDS TESTED CONCURRENTLY IN THE SAME ASSAY(S).
♦ DENOTES ITEM MEETING THE CRITERIA FOR SIGNIFICANCE
†RESULTS WITH ≥ 50% STIMULATION OR INHIBITION ARE BOLDFACED.
(NEGATIVE VALUES CORRESPOND TO STIMULATION OF BINDING OR ENZYME ACTIVITY)
R = ADDITIONAL COMMENTS
BOV = BOVINE; HUM = HUMAN

DICHLORINATED HETEROCYCLIC COMPOUNDS AND METHODS OF SYNTHESIS

This is a divisional application of patent application Ser. No. 10/281,563 filed Oct. 28, 2002 now U.S. Pat. No. 6,727,262 which claimed benefit, under 35 U.S.C. §119(e), to provisional application Ser. No: 60/361,146 filed on Mar. 1, 2002 under 35 U.S.C. 111(b).

FIELD OF THE INVENTION

The present invention teaches compositions comprising dichloro heterocyclic compounds and the synthesis of the same.

BACKGROUND

A variety of heterocyclic compounds have been described as having various pharmaceutical applications. However, the synthesis of such compounds, especially on a large scale, is often labor-intensive, expensive and time consuming. What is needed therefore, is a simplified and economical method for the synthesis and purification of halogenated heterocyclic compounds.

SUMMARY OF THE INVENTION

In one embodiment the present invention teaches a dichloro heterocyclic compound corresponding to 3-dichloromethylsulfinyl-7-fluoro-1-methyl-4-quinolone (dichloroflosequinan) and derivative thereof.

In another embodiment, the present invention contemplates a method for the synthesis so of 3-dichloromethylsulfinyl-7-fluoro-1-methyl-4-quinolone (dichloroflosequinan) comprising: a) providing, i) 3-dichloromethylthio-7-fluoro-1-methyl-4-quinolone, ii) dichloromethane (DCM), and iii) m-chloroperbenzoic acid (MCPBA); and b) reacting, i) 3-chloromethylthio-7-fluoro-1-methyl-4-quinolone, ii) dichloromethane (DCM), and iii) m-chloroperbenzoic acid ("MCPBA") under conditions such that 3-dichloromethylsulfinyl-7-fluoro-1-methyl-4-quinolone is produced.

In another embodiment, the present invention contemplates a method for the synthesis of 3-dichloromethylsulfinyl-7-fluoro-1-methyl-4-quinolone (dichloroflosequinan) comprising: a) providing the compounds comprising i) thionyl chloride, ii) pyridine, iii) 3-chloromethylsulfinyl-7-fluoro-1-methyl-4-quinolone (mono-chloroflosequinan), iv) dichloromethane (DCM), and v) m-chloroperbenzoic acid ("MCPBA"); and b) reacting said i) thionyl chloride, ii) pyridine, iii) 3-chloromethylsulfinyl-7-fluoro-1-methyl-4-quinolone (mono-chloroflosequinan), iv) dichloromethane (DCM), and v) m-chloroperbenzoic acid ("MCPBA") under conditions such that 3-dichloromethylsulfinyl-7-fluoro-1-methyl-4-quinolone is produced.

DEFINITIONS

As used herein, the phrase "flosequinan" refers to 7-fluoro-1-methyl-3-(methylsulphinyl)-4(1H)-quinolinone which may also be described as 7-fluoro-1-methyl-3-(methylsulfinyl)-4(1H)-quinolone) and as 7-fluoro-1-methyl-3-methylsulfinyl-4-quinolone having the chemical structure of:

As used herein dichloroflosequinan refers to the chemical composition designated as 3-dichloromethylsufinyl-7-fluoro-1-methyl-4-quinolone having the chemical structure corresponding to:

As used herein, "room temperature", "RT" or "ambient temperature" is approximately 18° C. to 25° C.

As used herein, "overnight" is approximately 8 hours, more preferably 12 hours, more typically 17 hours, but can be up to approximately 30 hours.

As used herein, a "heterocyclic" compound refers to a compound comprising a ring composed of atoms of more than one kind.

As used herein, a "catalyst" refers to a substance that, when added to a reaction mixture, changes (e.g. speeds up) the rate of attainment of equilibrium in the system without itself undergoing a permanent chemical change. Examples of suitable catalysts contemplated for use in the present invention include, but are not limited to, antimony chloride and carbon tetrabromide.

As used herein, a "solvent" refers to a substance that will dissolve other substances. An "organic solvent" is an organic substance that will dissolve other substances. Examples of solvents suitable for use in embodiments of the present invention include, but are not limited to dichloromethane and acetonitrile.

As used herein, the term "IBMX" corresponds to the structure having the chemical formula: 3-isobutyl-1-methylxanthine (available from Sigma).

DETAILED DESCRIPTION OF THE INVENTION

In one embodiment, the present invention describes a composition comprising dichloroflosequinan. In another embodiment, the present invention teaches methods for the synthesis of dichloroflosequinan.

The present invention also contemplates the formulation of dichloroflosequinan as a pharmaceutically acceptable salt.

In addition, pharmaceutical formulations of dichloroflosequinan may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of dichloroflosequinan as a pharmaceutically acceptable salt or formulation. The present invention also contemplates the administration of dichloroflosequinan and dichloroflosequinan formulations to a subject.

Methods of producing flosequinan, as set out in U.S. Pat. Nos. 5,079,264 and 5,011,931 to MacLean et al., are hereby incorporated by reference. In one embodiment, flosequinan is prepared according to the protocol set out in Example 2. Furthermore methods for the preparation on monochloroflosequinan (a starting reagent, in a preferred embodiment, for the synthesis of dichloroflosequinan) is prepared according to the protocol set out in Example 3.

Without limiting the invention to any particular mechanism, dichloroflosequinan is an enzyme inhibitor. In a specific example, dichloroflosequinan inhibits phosphodiesterases (herein after, "PDE"). This effect of dichloroflosequinan on enzyme activity, more particularly PDE, has utility in therapeutics.

The present invention also contemplates the formulation of dichloroflosequinan as a pharmaceutically acceptable salt. In addition, pharmaceutical formulations of dichloroflosequinan may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of dichloroflosequinan as a pharmaceutically acceptable salt or formulation. The present invention also contemplates the administration of dichloroflosequinan formulations to a subject.

Synthesis of Dichloroflosequinan

The present invention teaches compositions and methods for the synthesis of 3-dichloromethylsulfinyl-7-fluoro-1-methyl-4-quinolone (dichloroflosequinan).

It is not intended that the present invention be limited to any particular method for the synthesis of 3-dichloromethylsulfinyl-7-fluoro-1-methyl-4-quinolone (dichloroflosequinan). In one embodiment, 3-dichloromethylthio-7-fluoro-1-methyl-4-quinolone is prepared and then reacted to produce 3-dichloromethylsulfinyl-7-fluoro-1-methyl-4-quinolone (dichloroflosequinan) in the following two step reaction.

1. Step One 3-dichloromethylthio-7-fluoro-1-methyl-4-quinolone [Compound (2) of FIG. 1] was prepared by reacting of monochloroflosequinan (3-chloromethylsulfinyl-7-fluoro-1-methyl-4-quinolone) [Compound (1) of FIG. 1] with thionyl chloride ("SOCl$_2$") and pyridine at a low temperature. This mixture was stirred and cooled, thereby, producing a solid that was filtered off, washed, and dried under vacuum.

2. Step Two

Figure 1:
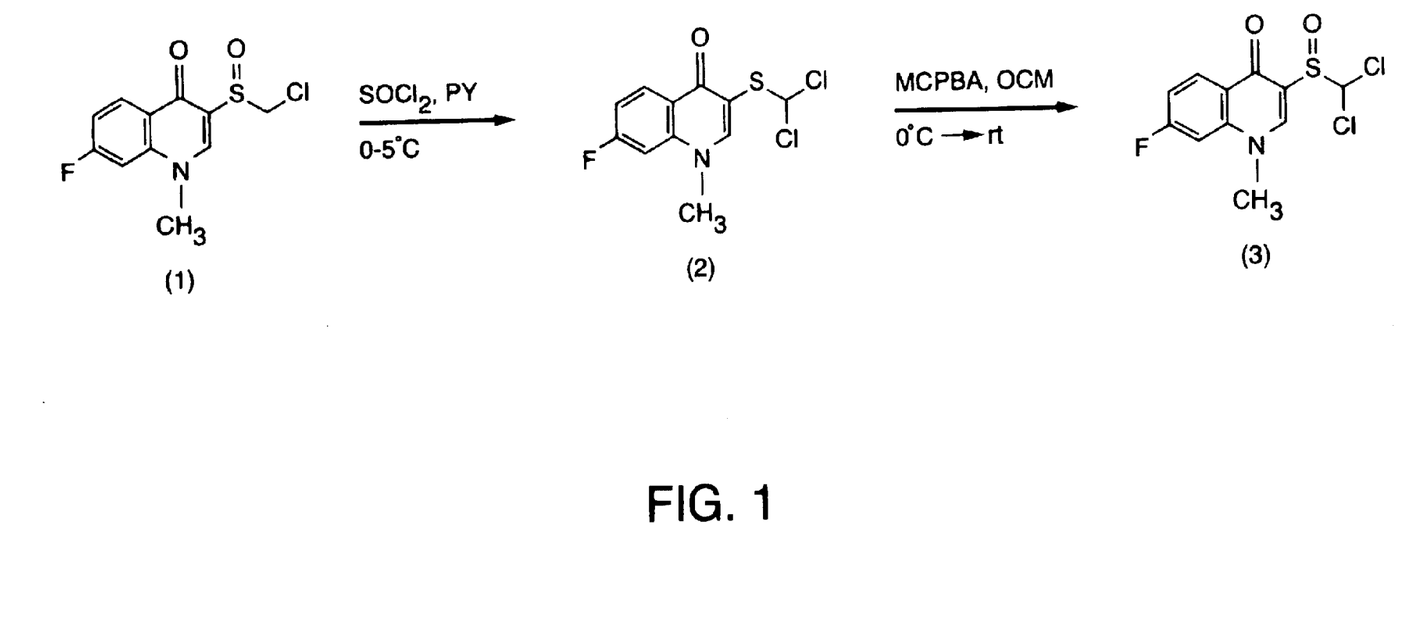
FIG. 1 shows a schematic protocol for the synthesis of dichloroflosequinan.

The 3-dichloromethylthio-7-fluoro-1-methyl-4-quinolone [Compound (2) of FIG. 1], prepared in step one, was then dissolved in dichloromethane ("DCM") and m-chloroperbenzoic acid ("MCPBA") at room temperature. This mixture was washed with Na$_2$CO$_3$, and the water layer was extracted with DCM.

The combined DCM solutions containing product were dried over Na$_2$SO$_4$ and concentrated to yield a final product of dichloroflosequinan.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); L (liters); ml (milliliters); ° C. (degrees Centigrade).

All bracketed numbers [e.g. "(1)"] after the chemical name of a compound, refer to the corresponding chemical structure as designated by the same bracketed number in FIG. 1.

All NMR spectra were recorded using Varian-Gemini 300 MHz Spectrometer.

In Examples 1–3, unless otherwise stated, the source for the chemical reagents was Aldrich, Milwaukee, Wis., USA (unless a reagent was synthesized de novo, as described in the examples). Flosequinan was synthesized according to the protocol provided in Example 2, unless specified otherwise.

EXAMPLE 1

This example describes one method for the synthesis of dichloroflosequinan. Briefly, 3-dichloromethylthio-7-fluoro-1-methyl-4-quinolone (i.e. Compound 2 of FIG. 1) is first prepared, and used as a reagent to produce 3-Dichloromethylsulfinyl-7-fluoro-1-methyl-4-quinolone (i.e. Compound 3 of FIG. 1) according to the following reactions.

A. 3-Dichloromethylthio-7-fluoro-1-methyl-4-quinolone (Compound 2 of FIG. 1)

To an efficiently stirred and gently cooled 4.2 ml mixture of thionyl chloride ("SOCl$_2$") and 1.05 ml of pyridine ("Py") at −3° C. was added 1.015 g (3.708 mmol) of 3-chloromethylsulfinyl-7-fluoro-1-methyl-4-quinolone (monochloroflosequinan)(Compound 1 of FIG. 1). This addition was made in multiple alloquots over a period of approximately 1 min. During this addition, cooling was applied to keep the temperature in the range 0–5° C.

This mixture was then stirred at 0° C. for 8 min and then cooled to −5° C. The mixture was then poured as a thin stream into, stirring, 120 ml of ice-water. After 10 minutes of stirring at 0° C., a solid was filtered off, washed with water, and dried over phosphorus pentoxide under high vacuum. [Yield: 669 mg (61.7%) of a crude product (i.e. Compound 2) that was approximately 94% pure by $^1$H NMR, CDCl$_3$; d=3.84 s, $^3$H, N—CH$_3$; 7.11 dd, $^1$H, J=10.0 & 2.2 Hz, H at C8, 7.19 ddd, $^1$H, J=8.9, 7.9 & 2.3 Hz, H at C6; 7.24 s, $^1$H, CHCl2; 8.03 s, $^1$H, H at C2; 8.47 dd, $^1$H, J=9.0 & 6.3 Hz, H at C5.]. This product was then, further, purified in Step B described below.

B. 3-Dichloromethylsulfinyl-7-fluoro-1-methyl-4-quinolone 665 mg (2.276 mmol) of the 3-dichloromethylthio-7-fluoro-1-methyl-4-quinolone (Compound 2, FIG. 1), as prepared in Step A, was dissolved in 20 ml of DCM at 0° C. to form a solution. To this solution was added 505.7 mg (2.345 mmol) of 80% MCPBA to form a mixture. This stirred mixture was then allowed to warm to room temperature and was stirred for 1 hour. An additional 25 mg of MCPBA was added and the mixture and stirred for 1 hour. The mixture was washed with 5% aqueous Na$_2$CO$_3$. The aqueous layer was extracted with DCM, and the combined DCM extracts were dried over anhydrous Na$_2$SO$_4$ and concentrated. The residue was chromatographed on silica gel with hexane-ethyl acetate (gradient 4:1,2:1,1:1) to give 352 mg (50%) of the product (Compound 3, FIG. 1) as a white solid, that was approximately 98% pure according to $^1$H NMR, CDCl$_3$;

d=3.96 s, $^3$H, N—CH$_3$; 7.09 s, $^1$H, CHCl$_2$; 7.22 dd, $^1$H, J=10.2 & 2.4 Hz, H at C8, 7.27 ddd, $^1$H, J=9.0, 7.6 & 2.2 Hz, H at C6; 8.03 s, $^1$H, H at C2; 8.43 dd, $^1$H, J=8.8 & 6.1 Hz, H at C5. This white solid product was further purified by recrystallization from methanol to give 252 mg of white crystals.

EXAMPLE 2

In this example flosequinan is prepared according to the following protocol:

A. Preparation of flosequinan i. Step I

In a clean and dry 12 L glass reactor equipped with a back suction trap plus a NaOH (25%) trap at the outlet and a back suction trap in the inlet, 3.840 L of toluene were charged and cooled to −45° C. using a dry ice-acetone bath. Using appropriate safety precautions, 832 g of phosgene were then passed through the cold toluene while stirring to prepare a 20% (wt/wt) solution. The addition of the phosgene took approximately 3.5 hours.

Separately, into a clean and dry 22 L glass reactor equipped with the above-described types of back suction traps, 399 g of starting material (formula I):

I was added with stirring to 4.37 L of deionized water. A separate 6.8% solution of sodium carbonate in water was also prepared by adding 297 g of sodium carbonate to 4.37 L of deionized water. Using a clean addition funnel, the sodium carbonate solution was then slowly added with stirring to the suspension of the starting material, to create a brown-colored solution.

In preparation for the reaction step, the phosgene solution was warmed from −45° C. to −15° C. and the mixture of the starting material and the sodium carbonate was cooled to 10° C. The phosgene solution was then added over approximately 1.5 hours with stirring to the brown solution. The reaction mixture was stirred overnight allowing the desired intermediate-A (formula II):

II to precipitate out. A sample was removed for NMR assessment and the precipitate was filtered on a 4 L sintered glass funnel. The filtrate was washed with 2×500 ml aliquots of cold deionized water and dried under a vacuum at approximately 50° C. for 16 hours.

A 93.4% lot yield of 435 g of intermediate-A (formula II) was obtained. This procedure was repeated three more times, starting with approximately 400 g of starting material each time. Lot yields of 448 g (94.5%), 449 g (95.9%), and 459 g (96.8%) were obtained.

ii. Step II

In a 22 L oven dried glass reactor equipped with a reflux condenser, addition funnel and temperature recorder, 11.40 L of anhydrous tetrahydrofuran (THF) were added under nitrogen. To this reactor were also added 409 g of 60% sodium hydride in oil. Eight approximately equal portions of intermediate-A (formula II) were then added to the reactor, totaling 883 g altogether. As this reaction is exothermic, care was taken to avoid excessive heat and bubbling. Final temperature was 40° C., with a maximum observed temperature of 41° C. The reaction mixture was stirred until hydrogen gas evolution ceased.

To the reaction mixture was then slowly added 575 ml (766.4 g) of dimethyl sulfate, keeping the temperature below 50° C. Upon completion, the reaction mixture was stirred at 50° C. for 3 hours with the reflux condenser on. A sample was removed for NMR assessment, and the heat was turned off before stirring overnight.

In the morning, the stirring was stopped and the clear liquid on top was siphoned off. This liquid was filtered using a 2–3 inch thick Celite pad in a 2 L sintered glass funnel. The residue cake was kept covered to minimize contact with atmospheric moisture. The residue was collected and washed with 4 aliquots of anhydrous THF. The filtrate and the washings were evaporated to dryness using a rotary evaporator and the residue obtained was dried under vacuum at approximately 36–38° C. overnight. A sample was removed for NMR assessment of the amount of unreacted dimethyl sulfate present. The dried residue was then added to 1600 ml of a 1:3 toluene:hexane mixture and vigorously stirred. This mixture was then filtered and washed with 2×700 ml washings of 1:3 toluene:hexane mixture. A reference sample was removed for NMR assessment and the residue was dried at 51–50° C. under vacuum for 36 hours.

This batch yielded 871 g of intermediate-B (formula III):

III for a lot yield of 91.6%. Another 907.1 g of intermediate-A was subjected to the procedure of step II, in which the amounts of reactants and solvents was proportionately adjusted with a yield of 850 g (87%).

iii. Step III

In an oven dried 12 L glass reactor equipped wvith a stirrer, temperature recorder and addition funnel 2550 ml of anhydrous toluene was added under nitrogen. Then 236 g of 60% sodium hydride in oil was added, all at room temperature. The reaction mixture was heated with continuous stirring to 75° C. using a heating mantel. Then 1.59 L of anhydrous dimethyl sulfoxide (DMSO) were added slowly and carefully over 45 minutes taking care to avoid excessive bubbling. The reaction mixture was stirred for one hour at 70–72° C. until clear and hydrogen gas evolution ceased. The heating mantel was turned off and a water bath was used to cool the reaction mixture to 30° C.

To this mixture, 538.2 g of dry intermediate-B (formula III) was added slowly in portions, keeping the temperature no higher than 35° C. Then 1.9 L of anhydrous DMSO was added, again keeping the temperature no higher than 35° C. The reaction mixture was stirred under nitrogen for one hour, allowing the mixture to cool to 26°. The reaction mixture was then quenched slowly and carefully with 320 ml of methanol. The resulting suspension was then added slowly and with vigorous stirring to a 22 L reaction vessel containing 12.760 L of diethyl ether.

After stirring was stopped, the upper ether layer was siphoned off and the brown oil lower layer was washed with 520 ml of fresh ether. The oily yellow residue was triturated with 2600 ml of deionized water until a yellow precipitate formed. This precipitate was filtered using a 2 L sintered glass funnel and the solid residue was washed with three aliquots of 130 ml cold deionized water. A reference sample was taken to assess the residue. The residue was dried under vacuum at 50–53° C. for 23 hours.

This procedure produced 243 g of intermediate C (formula IV):

which represents a 38.4% yield. Two other batches of intermediate-B were treated according to this Step III procedure, with proportionate adjustments to the amounts of reactants and solvents. The first additional batch of 538.2 g intermediate-B produced a 192 g (30.4%) yield, and the second additional batch of 87.38 g of intermediate-B produced a yield of 42 g (40.9%).

iv. Step IV

In a 12 L oven dry glass reactor equipped with a stirrer, temperature recorder and addition funnel which has been dried by nitrogen flow for 30 minutes the following chemicals were charged: 7.990 L of triethyl orthoformate; 696 g of intermediate-C; 324 ml of piperdine; and 296 ml of acetic acid. The reaction mixture was heated under nitrogen to reflux at approximately 105° C. for 2 hours. A sample was removed to assess the progress of the reaction step by NMR.

Using a water bath, the reaction mixture was then cooled to room temperature and stirred for 30 minutes. The final product precipitated out and was collected by filtration on a 4 L sintered glass funnel. The residue was washed with 3×700 ml aliquots of diethyl ether, and a sample was removed for NMR assessment. The residue was dried under vacuum at 50–51° C. for 17 hours. A sample of the dried flosequinan product (formula V):

was removed for NMR assessment. 547 g (75.3%) yield of flosequinan was obtained (an additional 47 g of product was scraped from the bottom of the sintered glass filter but was not included in this total yield calculation).

EXAMPLE 3

Figure 6:
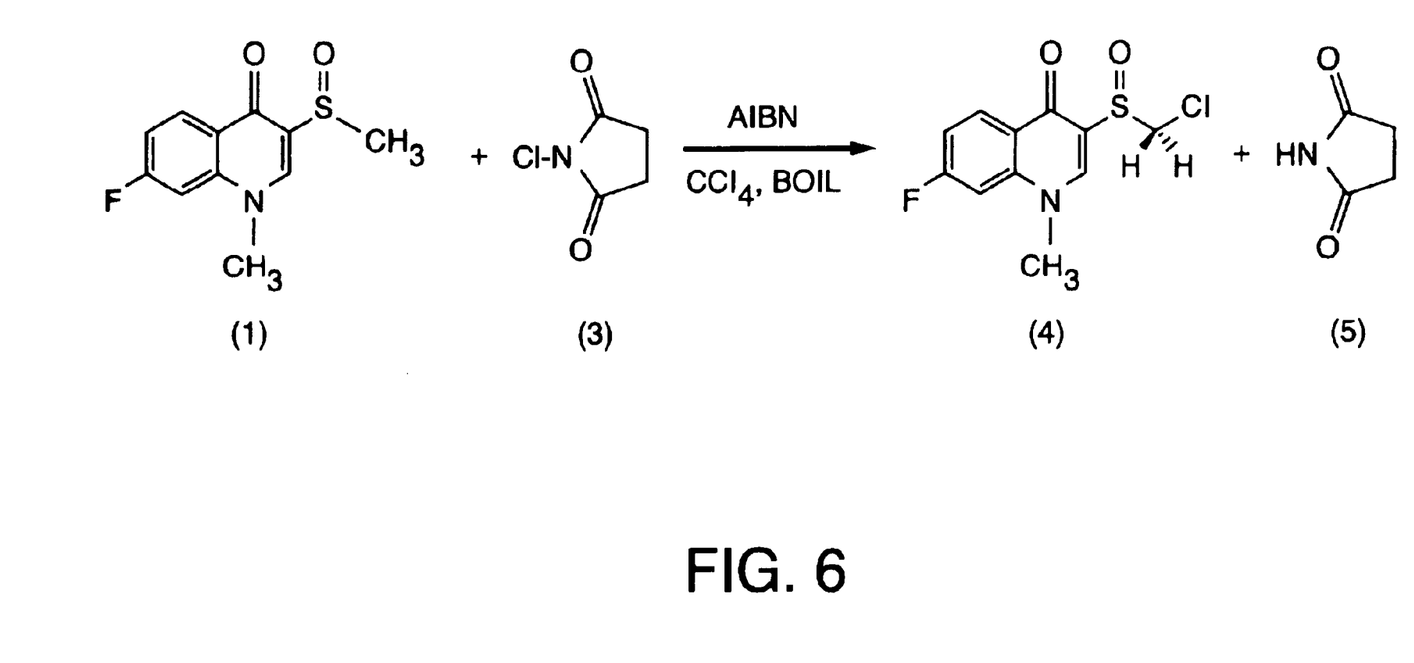
FIG. 6 projects the protocol for the direct chlorination of 7-fluoro-1-methyl-3-methylsulfinyl-4-quinolone (flosequinan).

This example presents a one-step protocol for the synthesis of 3-chloromethylsulfinyl-7-fluoro-1-methyl-4-quinolone (racemic monochloroflosequinan) via the direct chlorination of 7-fluoro-1-methyl-3-methylsulfinyl-4-quinolone (flosequinan) according to the synthetic scheme set out in FIG. 6. This overall synthesis is described in more detail according to the following reactions.

900 ml of anhydrous carbon tetrachloride and 25 g (0.015 mol) of 7-fluoro-1-methyl-3-methylsulfinyl-4-quinolone (1) (flosequinan) were placed in a two L, round bottom reaction flask (equipped with a mechanical stirrer, a reflux condenser with gas outlet adapter, a thermometer and a gas inlet adapter in the fourth neck). The reaction flask was then immersed in an oil bath preheated to 95° C. while nitrogen gas was flowed over the reaction mixture (which was gently agitated) at a rate sufficient to prevent the infiltration of air into the reaction mixture. Once this reaction mixture reached a gentle boil, a mixture of N-chlorosuccinimide, compound (3), (15.5 g; 0.116 mole) and 1.1 g of 2,2'-azobisisobutyronitrile (AIBN) was added in five equal portions over 15 minute intervals. The mixture was boiled for an additional 30 minutes. The flask was then cooled to ambient temperature and the precipitated product was collected via filtration through a sintered glass filter. The precipitate was then washed with 50 ml of water, followed by 50 ml of acetone and finally recrystallized from 2.5 L of acetone, yielding 4.416 g of yellow crystals. Another 2.225 g of the product were collected when the first filtrate was concentrated to a volume of 750 ml. In total, 6.64 g (23.1% yield) of 3-chloromethylsulfinyl-7-fluoro-1-methyl-4-quinolone (4) (racemic monochloroflosequinan), of greater than 98% purity (as determined by NMR) were obtained. 1H NMR, CDCl$_3$; δ=3.95 s, 3H, N—CH$_3$; 4.92 dd, 2H, J=11.1 & 7.8 Hz, CH$_2$; 7.18–7.29 m, 2H, H at C6 and C8; 7.95 s, 1H, H at C2; 8.42–8.47 m, 1H, H at C5.

EXAMPLE 4

In this example, dichloroflosequinan was subjected to biochemical enzyme assays to determine its respective percent inhibition of a variety of phosphodiesterases (PDE1-PDE6). The methods used have been adapted from those described in the scientific literature, see Hidaka and Asano "Human blood platelet 3':5' cyclic nucleotide phosphodiesterase. Isolation of low-Km and high Km phosphodiesterase." *Biochem. Biophys. Acta* 429:485 (1976); Nicholson et al. "Differential modulation of tissue function and therapeutic potential of selective inhibitors of cyclic nucleotide phosphodiesterase isoenzymes" *Trends Pharmacol. Sci.* 12:19 (1991); Cortijo et al. "Investigation into the role of phosphodiesterase IV in bronchorelaxation, including studies with hyman bronchus." *Br. J. Pharmacol.* 108:562 (1993); Baehr et al. "Isolation and characterization of cGMP phosphodiesterase from bovine rod outer segments." *J. Biol. Chem.* 254:11669 (1979) and Gillespie and Beavo "Inhibition and stimulation of photoreceptor phosphodiesterase by dipyridamole and M&B 22,948" *Molecular Pharm.* 36:773 (1989). A brief summary of the conditions for each enzyme assay is provided below:

PDE1: PDE1 partially purified from bovine heart was used. The compounds were independently incubated with 13 μg PDE1 enzyme, 1.01 μM [$^3$H]cAMP+cAMP and CaCl$_2$/calmodulin in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE2: PDE2 partially purified from human platelets was used. The compounds were independently incubated with 23 μg PDE2 enzyme, 25.1 μM [$^3$H]cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE3: PDE3 partially purified from human platelets was used. The compounds were independently incubated with 13 μg PDE3 enzyme and 1.01 μM [$^3$H]cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE4: PDE4 partially purified from human U-937 pronocytic cells was used. The compounds were independently incubated with 20 μg PDE4 enzyme and 1.01 μM [$^3$H] cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE5: PDE5 partially purified from human platelets was used. The compounds were independently incubated with 120 μg PDE5 enzyme and 1.01 μM [$^3$H]cGMP+cGMP in Tris buffer pH 7.5 for 20 minutes at either 25° C. or 30° C. The reaction was terminated by boiling for 2 minutes, and the resulting GAP was converted to guanosine by addition of 10 mg/ml snake venom nucleotidase and further incubation at 30° C. for 10 minutes. Unhydrolyzed cGMP was bound to AGI-X2 resin, and the remaining [$^3$H]guanosine in the aqueous phase was quantitated by scintillation counting.

PDE6: PDE6 partially purified from bovine retinal rod outer segments and activated by trypsin was used. The compounds were independently incubated with 0.2 μg/ml active PDE6 and 100 μM [$^3$H]cGMP+cGMP in Tris buffer pH 7.5 for 20 minutes at either 25° C. or 30° C. Each reaction was terminated by boiling for 2 minutes. The resulting GAP was converted to guanosine by addition of 10 mg/ml snake venom nucleotidase, and further incubated at 30° C. for 10 minutes. Unhydrolyzed cGMP was bound to AGI-X2 resin, and [$^3$H]guanosine remaining in the aqueous phase was quantitated by scintillation counting.

Figure 2A:
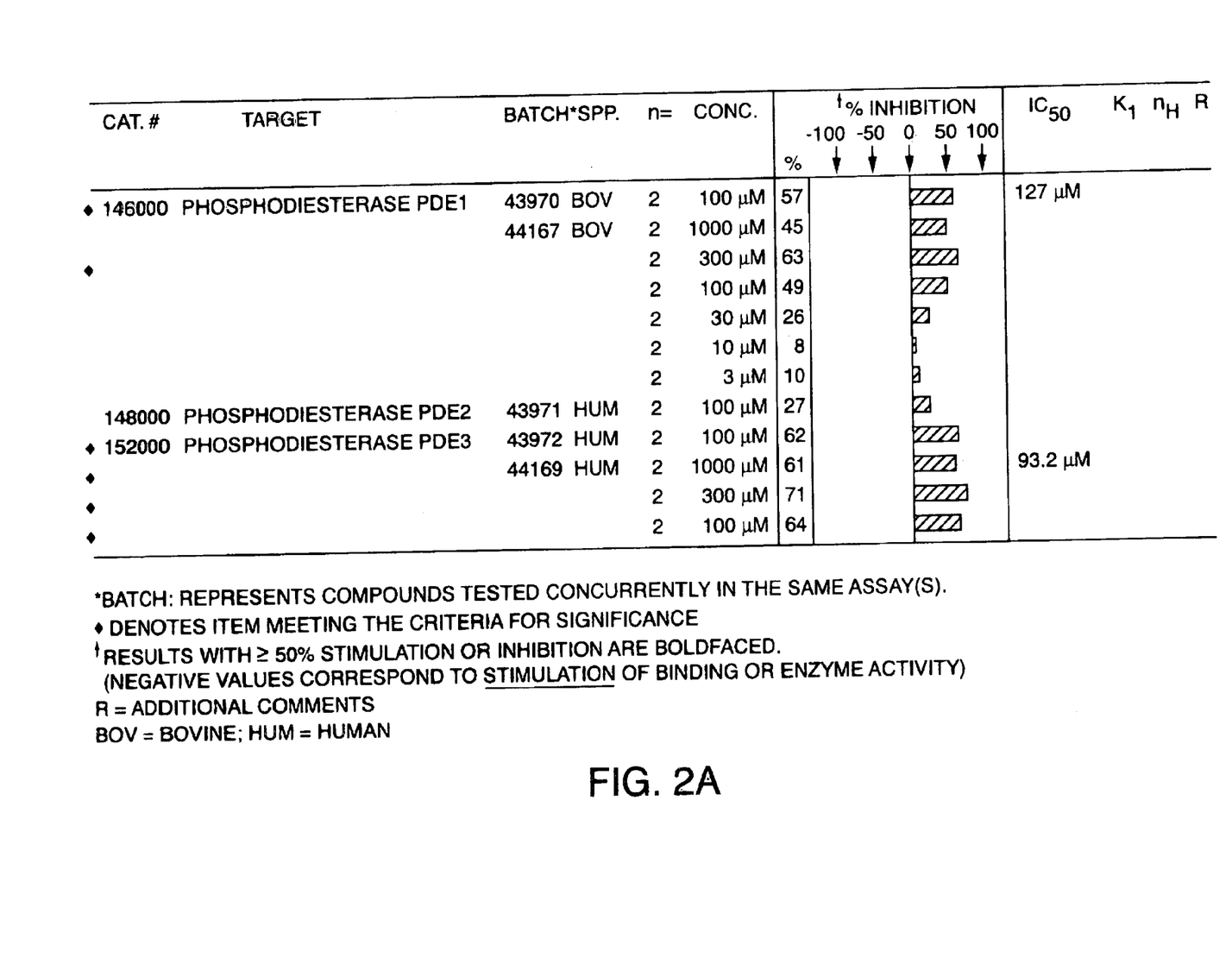
FIG. 2 depicts the results of in vitro PDE enzyme inhibition assays using dichloroflosequinan.
Figure 2B:
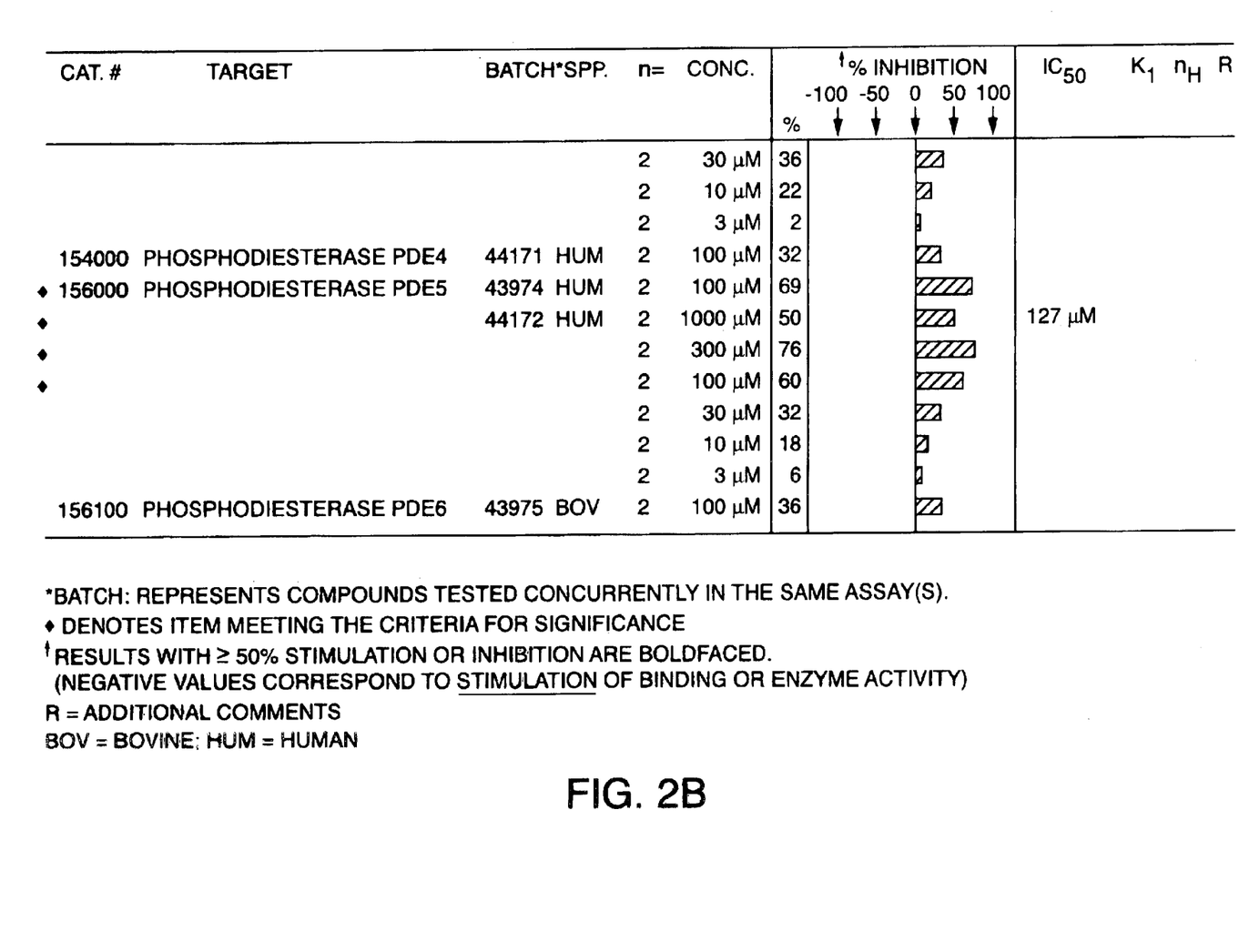

FIG. 2 shows the results of assays carried out as described above with dichloroflosequinan. Each PDE was assayed at 25° C. with varying concentrations of dichloroflosequinan (in 1% DMSO as the vehicle). Significant inhibition (e.g. greater than 50% inhibition) of PDE1, PDE3, and PDE5 was observed.

Figure 3:
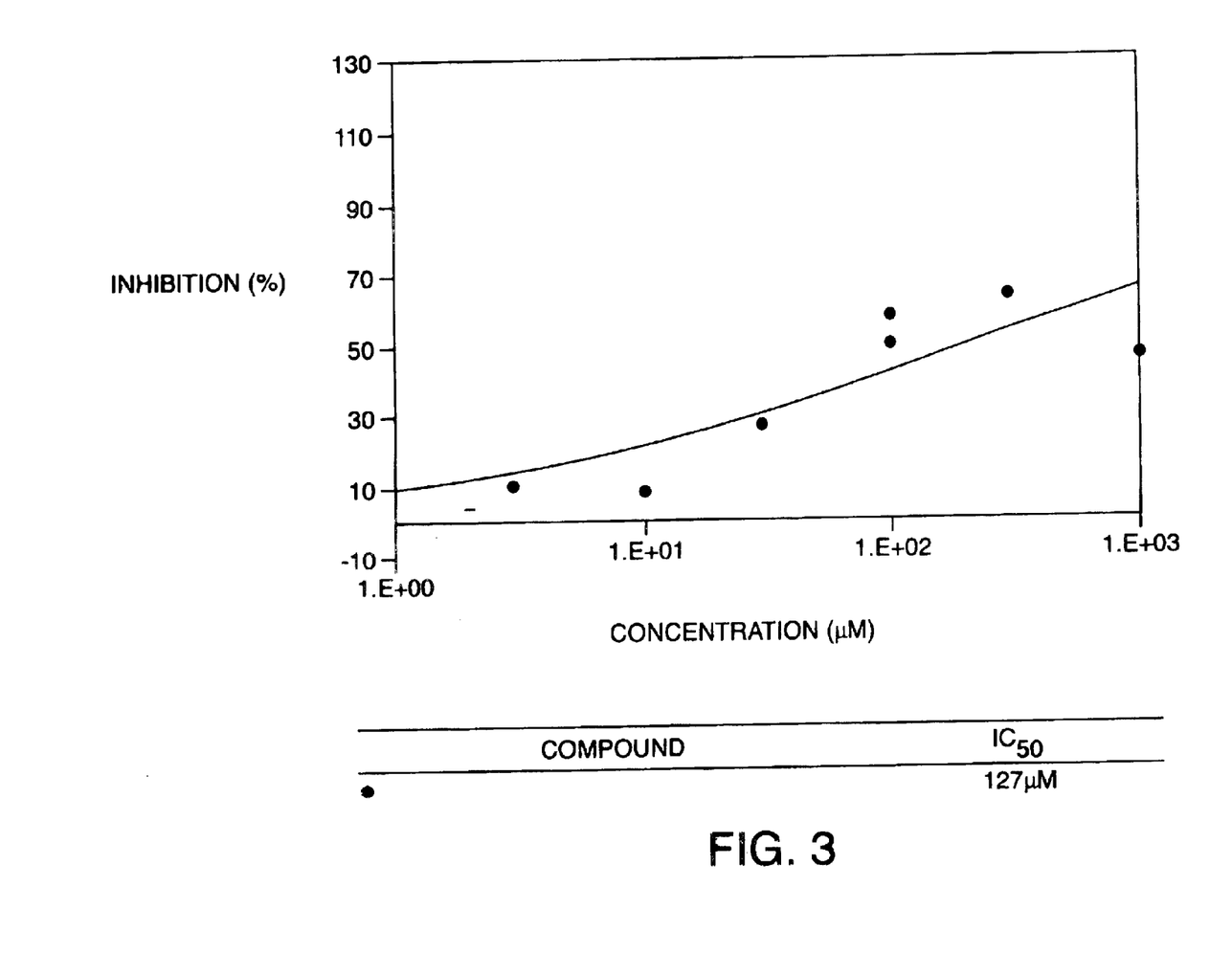
FIG. 3 shows the PDE1 inhibition curves for dichloroflosequinan (circles).

FIG. 3 shows the inhibition curves for PDE1 for dichloroflosequinan (circles).

Figure 4:
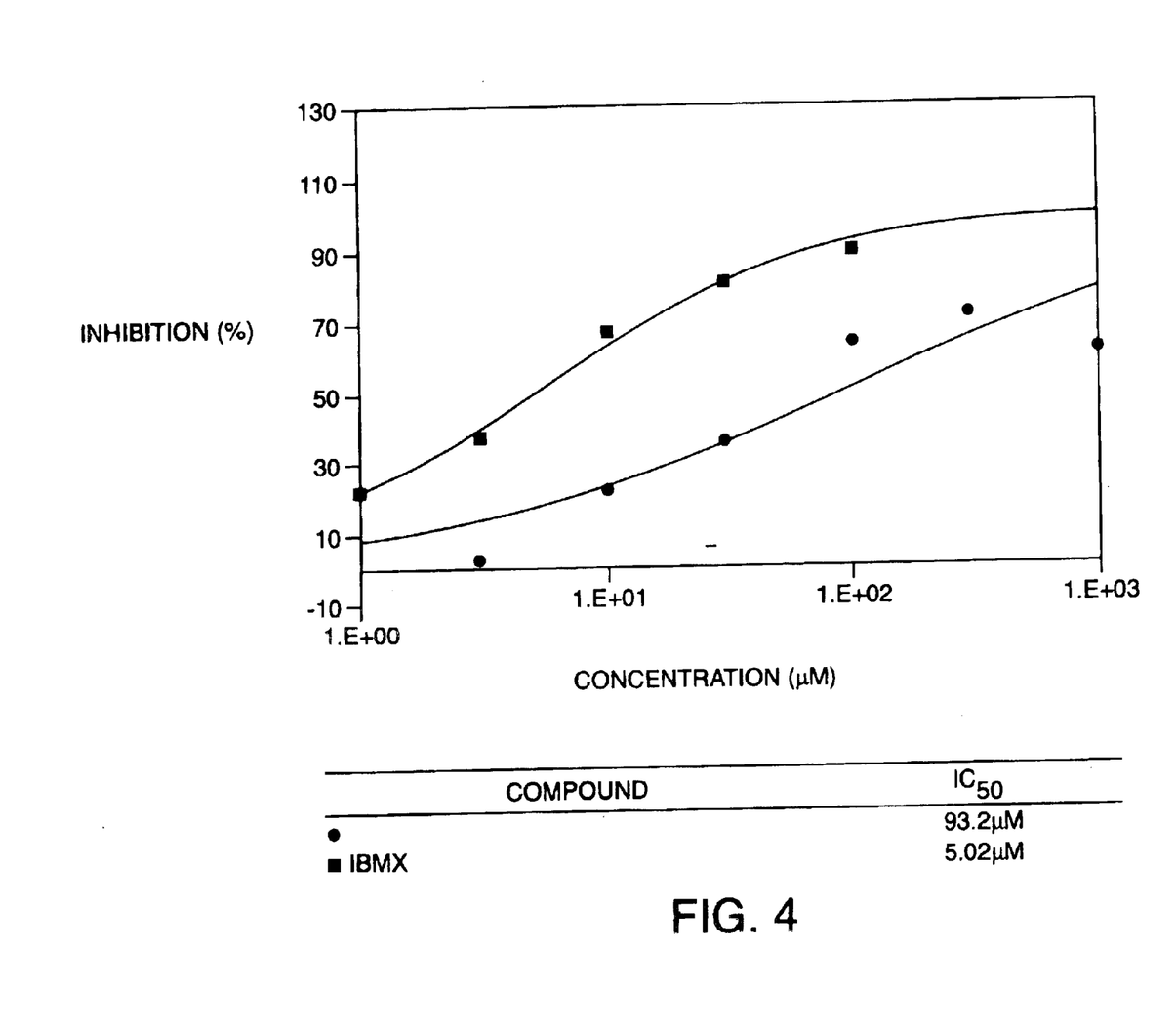
FIG. 4 shows the PDE3 inhibition curves for dichloroflosequinan (circles) and the reference compound, IBMX (squares).

FIG. 4 shows the inhibition curves for PDE3 for dichloroflosequinan (circles) and the reference compound, IBMX (squares).

Figure 5:
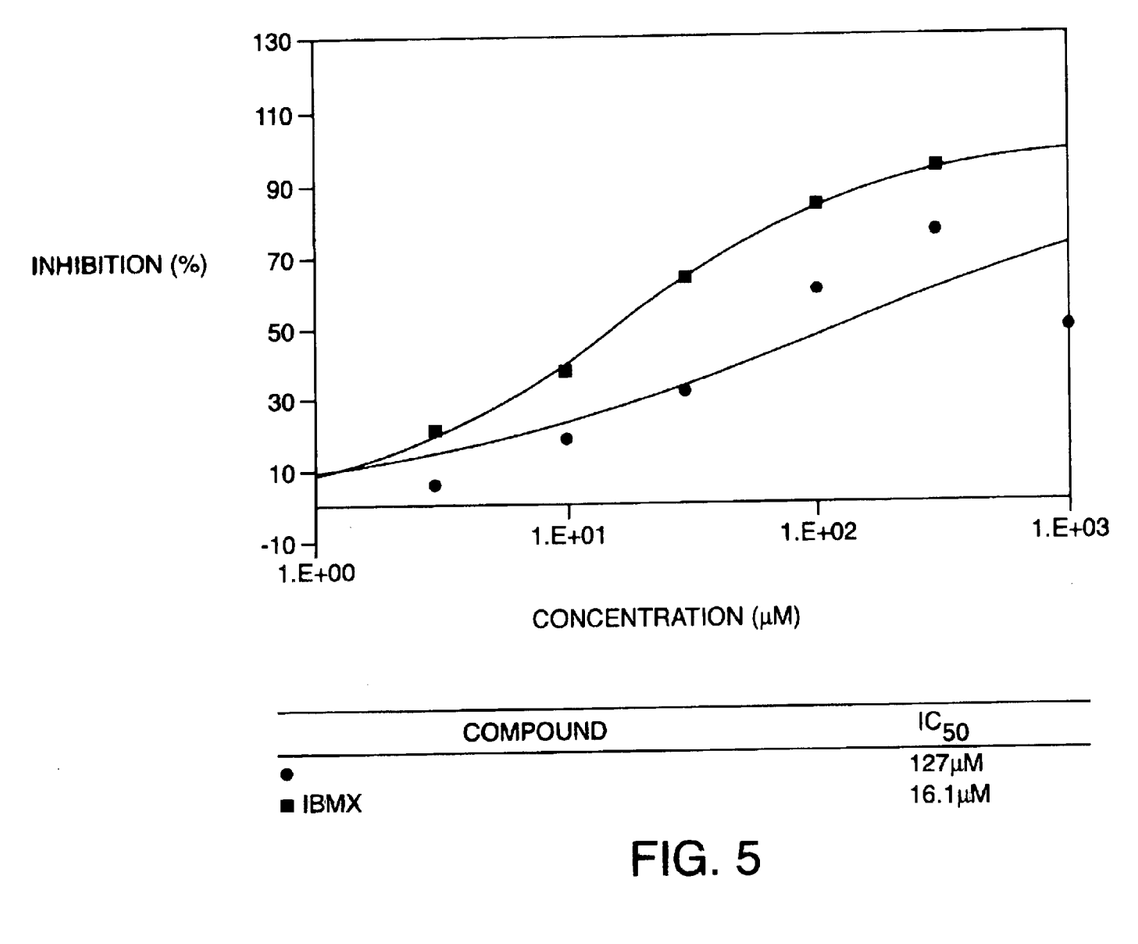
FIG. 5 shows the PDE5 inhibition curves for dichloroflosequinan (circles) and the reference compound, IBMX (squares).

FIG. 5 shows the inhibition curves for PDE5 for dichloroflosequinan (circles) and the reference compound, IBMX (squares).

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method for the production of 3-dichloromethylsulfinyl-7-fluoro-1-methyl-4-quinolone, comprising:
    a) providing:
        i) 3-dichloromethylthio-7-fluoro-1-methyl-4-quinolone;
        ii) dichloromethane; and
        iii) m-chloroperbenzoic acid;
    b) reacting said 3-dichloromethylthio-7-fluoro-1-methyl-4-quinolone, dichloromethane, and m-chloroperbenzoic acid under conditions such that 3-dichloromethylsulfinyl-7-fluoro-1-methyl-4-quinolone is produced.

* * * * *